(12) United States Patent
Muir

(10) Patent No.: US 7,009,072 B2
(45) Date of Patent: Mar. 7, 2006

(54) METHOD FOR PRODUCING LUBRICANT DETERGENTS

(75) Inventor: Ronald J. Muir, West Hill (CA)

(73) Assignee: Crompton Corporation, Middlebury, CT (US)

( * ) Notice: Subject to any disclaimer, the term of this patent is extended or adjusted under 35 U.S.C. 154(b) by 22 days.

(21) Appl. No.: 10/674,896

(22) Filed: Sep. 29, 2003

(65) Prior Publication Data

US 2004/0097750 A1    May 20, 2004

Related U.S. Application Data

(60) Provisional application No. 60/422,493, filed on Oct. 31, 2002.

(51) Int. Cl.
*C07C 65/10* (2006.01)
*C07C 65/05* (2006.01)
*C07C 65/03* (2006.01)
*C07C 65/01* (2006.01)

(52) U.S. Cl. .................................................. 562/477

(58) Field of Classification Search ................ 562/477
See application file for complete search history.

(56) References Cited

U.S. PATENT DOCUMENTS

| | | | |
|---|---|---|---|
| 1,998,750 A | 4/1935 | Bruson et al. | 260/111 |
| 2,490,444 A | 12/1949 | Kooljman et al. | 260/521 |
| 2,865,956 A | 12/1958 | Ellis et al. | 260/504 |
| 3,337,616 A | 8/1967 | Keeding et al. | 260/521 |
| 3,410,798 A | 11/1968 | Cohen | 252/37.2 |
| 3,438,899 A | 4/1969 | Benoit, Jr. | 252/51.5 |
| 3,557,198 A | 1/1971 | Yekimik | 260/521 |
| 3,853,956 A | 12/1974 | Schmerling | 260/473 |
| 3,884,949 A | 5/1975 | Eicke et al. | 260/429.3 |
| 4,060,535 A | 11/1977 | Cinco | 260/414 |
| 4,544,491 A | 10/1985 | Tyson et al. | 210/772 |
| 4,810,398 A | 3/1989 | Van Kruchten et al. | 252/40 |
| 4,869,837 A * | 9/1989 | van Wijngaarden et al. | 508/460 |
| 4,876,020 A | 10/1989 | Zon et al. | 252/40.5 |
| 4,910,334 A | 3/1990 | Stuart et al. | 562/96 |
| 5,030,687 A * | 7/1991 | Leone | 508/460 |
| 5,049,685 A | 9/1991 | Saito | 556/132 |
| 5,225,588 A | 7/1993 | Senaratne et al. | 560/71 |
| 5,259,966 A | 11/1993 | Burke et al. | 252/18 |
| 5,415,792 A | 5/1995 | Campbell | 252/18 |
| 5,434,293 A * | 7/1995 | Campbell | 560/71 |
| 5,451,331 A | 9/1995 | O'Connor et al. | 252/18 |
| 5,538,650 A | 7/1996 | Goto et al. | 508/331 |
| 5,652,203 A | 7/1997 | Asamori et al. | 508/460 |
| 5,734,078 A | 3/1998 | Feilden et al. | 562/477 |
| 5,792,735 A | 8/1998 | Cook et al. | 508/452 |
| 6,034,039 A | 3/2000 | Gomes et al. | 508/331 |
| 6,281,179 B1 | 8/2001 | Skinner et al. | 510/184 |
| 6,348,438 B1 | 2/2002 | Le Coent et al. | 508/332 |
| 6,417,148 B1 | 7/2002 | Skinner et al. | 510/184 |
| 6,429,178 B1 | 8/2002 | Skinner et al. | 510/184 |
| 6,429,179 B1 | 8/2002 | Skinner et al. | 510/184 |

FOREIGN PATENT DOCUMENTS

| | | |
|---|---|---|
| CH | 206596 | 8/1939 |
| DE | 689600 | 4/1940 |
| DE | 269619 | 7/1989 |
| DE | 293108 | 8/1991 |
| EP | 0351052 | 6/1989 |
| EP | 0370389 A2 | 5/1990 |
| EP | 0771782 A1 | 5/1997 |

* cited by examiner

Primary Examiner—Elvis O. Price
(74) Attorney, Agent, or Firm—Michael P. Dilworth

(57) ABSTRACT

The invention is a process for producing alkaline earth metal salicylates for use as lubricant detergents and to compositions prepared by the process. The process comprises two steps. Step 1 is the alkylation of salicylic acid is conducted using $C_{14}$ or greater linear α-olefins to produce alkyl salicylic acids in commercially acceptable yields. The alkylation conditions produce predominately mono-substituted para alkyl salicylic acids that are oil soluble. Step 2 is the oil soluble acid is subsequently neutralized and overbased by carbonation of lime using $CO_2$ in the presence of a promoter and a surfactant. The reaction mixture after overbasing is filtered and solvents are removed by distillation. Alternatively, alkyl salicylic acid can be reacted with a previously overbased alkaline earth sulfonate, e.g., calcium sulfonate, to produce alkaline earth salicylate salts comprising varying percentages of dispersed alkaline earth carbonate salts. In this method, no filtration of the end product is required, and, thus, it is commercially preferred.

9 Claims, No Drawings

METHOD FOR PRODUCING LUBRICANT DETERGENTS

I claim the benefit under Title 35, United States Code, § 120 to U.S. Provisional Application No. 60/422,493, filed Oct. 31, 2002, entitled METHOD FOR PRODUCING LUBRICANT DETERGENTS.

BACKGROUND OF THE INVENTION

1. Field of the Invention

The present invention relates to a method for producing alkaline earth overbased detergents for use in lubricants.

2. Description of Related Art

It is known to use alkaline earth metal salts of organic carboxylic acids as additives for lubricating oil compositions. These salts have a dispersant property that helps ensure that the insides of engine cylinders remain clean and that deposition of carbonaceous products on pistons and in piston grooves is counteracted, thus preventing piston-ring sticking.

It is also known to prepare basic (or overbased) alkaline earth metal salts of such acids. The overbasing provides an alkaline reserve which, when applied in lubricating oil compositions, reacts with and neutralizes acidic compounds formed during the operation of the engine in which the composition is applied. Hence, any sludge that may arise is dispersed owing to the dispersant property of the salt, while acids that would enhance sludge formation are neutralized.

Overbased salicylates are prepared by overbasing the corresponding alkylated salicylic acids. The alkyl group is typically a long chain alkyl group of greater than about 14 carbon atoms so as to impart oil solubility. Alkylated salicylic acids are conventionally prepared by the alkylation of a phenol to form an alkylphenol followed by carboxylation of the alkylphenol by the Kolbe-Schmitt reaction to provide the alkylated salicylic acid. In addition to the adverse economics attributable to the use of high temperatures and/or pressures, the Kolbe-Schmitt route to alkylated salicylic acids suffers from the problem that, when substantially linear alkylation feeds are employed, not all of the long-chain alkylphenol is readily carboxylated. Specifically, conventional alkylation of phenol with a substantially linear alkylation feed provides for approximately a 50:50 mixture of ortho-alkylphenol and para-alkylphenol. While the Kolbe-Schmitt reaction readily carboxylates the resulting long chain para-alkylphenol, the resulting long chain ortho-alkylphenol is less reactive and only about 70 percent of the total amount of the alkylphenol derived from a substantially linear alkylation feed is typically converted to alkylated salicylic acid during this reaction.

One method of circumventing this problem is to alkylate an alkyl salicylate (e.g., methyl salicylate) and then subject the resulting alkylated alkyl salicylate to hydrolysis so as to provide for the alkylated salicylic acid. Methods of alkylating alkyl salicylates are disclosed in U.S. Pat. No. 5,434,293.

DD-A-269 619 and DD-A-293 108 both disclose the direct alkylation of salicylic acid with an olefin using an acidic ion exchange resin or polyphosphoric acid respectively as catalyst. Both documents teach that the use of sulphuric acid as a catalyst (in prior art processes not involving alkylation of the acid with an olefin) is undesirable because it has many disadvantages, such as corrosion problems and side reactions.

DE 689 600 discloses the use of perchloric acid as the catalyst.

U.S. Pat. No. 1,998,750 discloses the condensation of salicylic acid with any nonaromatic monohydric alcohol having from 5 to 7 carbon atoms, or with compounds capable of furnishing an amyl-, hexyl-, cyclohexyl-, or heptyl-group, in the presence of sulfuric acid.

U.S. Pat. No. 4,810,398 discloses a basic alkaline earth metal salt of a blend of organic carboxylic acids is prepared by (a) preparing a mixture of one equivalent of the blend of organic carboxylic acids and more than one equivalent of an alkaline earth metal hydroxide and/or oxide in a hydrocarbon solvent; (b) introducing carbon dioxide into the mixture obtained in an amount of at least 0.5 equivalent carbon dioxide per equivalent of excess alkaline earth metal; and (c) removing residual solids, if any, and an aqueous layer, if any, whereby the blend of organic carboxylic acids comprises a $C_{8-30}$ alkyl salicylic acid and one or more alkanecarboxylic acids in which the alkyl moiety is branched and has from 4 to 40 carbon atoms. Such a salt has dispersant properties and is said to be suitable for use in lubricating oil and fuel compositions.

U.S. Pat. No. 4,869,837 discloses a process for the preparation of a basic alkaline earth metal salt of a blend of organic carboxylic acids, which comprises (a) preparing a mixture of one equivalent of the blend of organic carboxylic acids and more than one equivalent of an alkaline earth metal hydroxide and/or oxide in a hydrocarbon solvent; (b) introducing carbon dioxide into the mixture obtained in an amount of at least 0.5 equivalent carbon dioxide per equivalent of excess alkaline earth metal; and (c) removing residual solids, if any, and an aqueous layer, if any, whereby the blend of organic carboxylic acids comprises an oil-soluble alkyl salicylic acid and one or more hydrocarbon substituted succinic acids or anhydrides, in which the hydrocarbon radical has a number average molecular weight from 120 to 5000.

U.S. Pat. No. 4,876,020 discloses a lubricating oil composition comprising a lubricating base oil, one or more overbased alkaline earth metal salts of an aromatic carboxylic acid, and a stabilizing agent which has been selected from a polyalkoxylated alcohol having a molecular weight from 150 to 1500.

U.S. Pat. No. 5,049,685 discloses a nuclear substituted salicylic acid represented by the following general formula

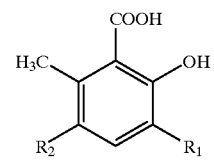

wherein $R_1$ represents a methyl group, an isopropyl group, a tert-butyl group, a tert-amyl group, a tert-hexyl group, a tert-octyl group, an $\alpha,\alpha$-dialkylbenzyl group or a nuclear substituted $\alpha,\alpha$-dialkylbenzyl group; and $R_2$ represents a tert-butyl group, a tert-amyl group, a tert-hexyl group, a tert-octyl group, an $\alpha,\alpha$-dialkylbenzyl group or a nuclear substituted $\alpha,\alpha$-dialkylbenzyl group) and a salt thereof The nuclear substituted salicylic acids and salts thereof are said to have good solubility in water, organic solvents or organic polymeric compounds and that they are very favorable as bactericidal and germicidal agents, stabilizers for polymeric compounds or color developing agents for recording materials.

U.S. Pat. No. 5,415,792 discloses overbased alkyl salicylates that are said to be useful additives for lubricating oil compositions. In particular, the compositions impart detergency and dispersancy to the lubricating oil composition as well as provide for an alkalinity reserve.

U.S. Pat. No. 5,434,293 discloses a method for alkylating alkyl salicylates using a solid acidic alkylation catalyst and approximately equimolar amounts of alkyl salicylate and alkylating feedstock.

U.S. Pat. No. 5,451,331 discloses a process for the production of a lubricating oil additive concentrate having a TBN greater than 300 that comprises reacting, at elevated temperature, component (A) a defined salicylic acid derivative, component (B) an alkaline earth metal base added either in a single addition or in a plurality of additions at intermediate points during the reaction, component (C) at least one compound which is (i) water, (ii) a polyhydric alcohol having 2 to 4 carbon atoms, (iii) a di- ($C_3$ or $C_4$) glycol, (iv) a tri- ($C_2$–$C_4$) glycol, (iv) a mono- or polyalkylene glycol alkyl ether of the formula (I) $R(OR^1)_x OR^2$ (I) wherein R is a $C_1$ to $C_6$ alkyl group, $R^1$ is an alkylene group $R^2$ is hydrogen or a $C_1$ to $C_6$ alkyl group and x is an integer from 1 to 6, (vi) a $C_1$ to $C_{20}$ monohydric alcohol, (vii) a $C_1$ to $C_{20}$ ketone, (viii) a $C_1$ to $C_{10}$ carboxylic acid ester, or (ix) a $C_1$ to $C_{20}$ ether, component (D) a lubricating oil, component (E) carbon dioxide added subsequent to the, or each, addition of component (B), component (F) a defined carboxylic acid or derivative, and component (G) at least one compound which is (i) an inorganic halide of (ii) an ammonium alkanoate or mono-, di-, tri- or tetra-alkyl ammonium formate or alkanoate provided that, when component (G) is (ii), component (F) is not an acid chloride, the weight ratios of all components being such as to produce a concentrate having a TBN greater than 300.

U.S. Pat. No. 5,734,078 discloses a process for the production of an alkyl salicylic acid in which the alkyl substituent has at least 6 carbon atoms, comprising reacting salicylic acid with an olefin having at least 6 carbon atoms at elevated temperature in the presence of sulphuric acid as a catalyst. Lubricating oil additives comprising a metal salt of such alkylated salicylic acids and a process for making them are also disclosed.

U.S. Pat. No. 5,792,735 discloses a lubricating oil composition said to be suitable for use in low or medium speed diesel engines that comprises a fuel oil with a residual oil content characterized in that the lubricating oil composition further comprises a hydrocarbyl-substituted phenate concentrate having a TBN greater than 300, and at least one of a hydrocarbyl-substituted salicylate and a hydrocarbyl-substitute sulphonate. The hydrocarbyl-substituted phenate is preferably one modified by incorporation of a carboxylic acid of the formula $RCH(R_1)CO_2H$ where R is a $C_{10}$–$C_{24}$ alkyl group and $R_1$ is hydrogen or a $C_1$ to $C_4$ alkyl group, e.g., stearic acid.

U.S. Pat. No. 6,034,039 discloses complex detergents that are said to provide improved deposit control and corrosion protection in crankcase lubricants.

The disclosures of the foregoing are incorporated herein by reference in their entirety.

SUMMARY OF THE INVENTION

The present invention is directed to a process for producing alkaline earth metal salicylates for use as lubricant detergents and to compositions prepared by the process. The process comprises two steps:

Step 1:
Alkylation of salicylic acid is conducted using $C_{14}$ or greater linear α-olefins to produce alkyl salicylic acids in commercially acceptable yields. The alkylation conditions produce predominately mono-substituted para alkyl salicylic acids that are oil soluble.

Step 2:
The oil soluble acid is subsequently neutralized and overbased by carbonation of lime using $CO_2$ in the presence of a promoter, such as methanol, and a surfactant, e.g., alkyl salicylic acid. The reaction mixture after overbasing is filtered and solvents are removed by distillation.

Alternatively, alkyl salicylic acid can be reacted with a previously overbased detergent selected from the group consisting of overbased alkali or alkaline earth sulfonates, phenates, or carboxylates, to produce alkali or alkaline earth salicylate salts comprising varying percentages of dispersed alkali or alkaline carbonate salts. In this method no filtration of the end product is required, and, thus, it is commercially preferred. It is also preferred that the overbased detergent be a previously overbased alkaline earth sulfonate, e.g., calcium sulfonate.

It has been shown that the olefin composition plays a role in the final products' performance in both pressure differential scanning calorimetry (PDSC) and in detergent additive compatibility and oil solubility. The preferred chain length is $C_{16}$ to $C_{18}$ for optimum PDSC, while higher $C_{18}$ content results in improved additive compatibility and solubility.

More particularly, the present invention is directed to a process for producing alkaline earth metal salicylates comprising the steps of:

A) alkylating salicylic acid with a linear (α-olefin comprising at least 14 carbon atoms in the presence of a strong acid catalyst to form an oil soluble alkylated salicylic acid;

B) neutralizing the oil soluble alkylated salicylic acid;

C) overbasing the oil soluble alkylated salicylic acid by carbonation of lime using $CO_2$ in the presence of a promoter and a surfactant;

D) filtering the product of C); and

E) removing solvents by distillation.

In another aspect, the present invention is directed to a process for producing alkali metal or alkaline earth metal salicylates comprising the steps of:

A) alkylating salicylic acid with a linear α-olefin comprising at least 14 carbon atoms in the presence of a strong acid catalyst to form an oil soluble alkylated salicylic acid;

B) reacting the oil soluble alkylated salicylic acid with a previously overbased detergent selected from the group consisting of overbased alkali or alkaline earth sulfonates, phenates, or carboxylates, e.g., calcium sulfonate, to produce alkali or alkaline earth salicylate.

In still another aspect, the present invention is directed to an alkaline earth metal salicylate produced by a process comprising the steps of:

A) alkylating salicylic acid with a linear α-olefin comprising at least 14 carbon atoms in the presence of a strong acid catalyst to form an oil soluble alkylated salicylic acid;

B) neutralizing the oil soluble alkylated salicylic acid;

C) overbasing the oil soluble alkylated salicylic acid by carbonation of lime using $CO_2$ in the presence of a promoter and a surfactant;

D) filtering the product of C); and

E) removing solvents by distillation.

In yet another aspect, the present invention is directed to an alkali metal or alkaline earth metal salicylate produced by a process comprising the steps of:

A) alkylating salicylic acid with a linear α-olefin comprising at least 14 carbon atoms in the presence of a strong acid catalyst to form an oil soluble alkylated salicylic acid;

B) reacting the oil soluble alkylated salicylic acid with a previously overbased detergent selected from the group consisting of overbased alkali or alkaline earth sulfonates, phenates, or carboxylates, e.g., calcium sulfonate, to produce alkali or alkaline earth salicylate salts comprising varying percentages of dispersed alkali or alkaline earth carbonate salts.

DESCRIPTION OF THE PREFERRED EMBODIMENTS

As noted above, the first step in the process of the present invention comprises the alkylation of salicylic acid using $C_{14}$ or greater linear α-olefins to produce alkyl salicylic acids in commercially acceptable yields. The alkylation conditions produce predominately mono-substituted para alkyl salicylic acids that are oil soluble.

The alkyl salicylic acids are prepared from salicylic acid and linear α-olefins using a strong acid, preferably anhydrous methanesulfonic acid, as the catalyst. Other strong acids that can be used include, for example, sulfuric, hydrochloric, nitric, trifluoroacetic, perchloric, and the like. The conditions are such as to allow a suspension of salicylic acid in the olefin to react at a temperature in the range of from about 120 to about 150° C. The products are mixtures of ortho and para monoalkylated salicylic acids with some dialkylated and trialkylated salicylic acids. The alkyl phenol content is very low and the color of the product is excellent compared to that obtained via the Kolbe-Schmitt synthesis. The alkylated salicylates have acid numbers that are approximately 85–95% of the theoretical value. PDSC and panel coker values of the corresponding overbased calcium salts of these salicylic acids are comparable or superior to control commercial salicylate detergents.

The alkyl salicylic acid used in the process of the present invention is rendered oil-soluble by the alkyl substituent or substituents it contains. It is possible that the alkyl salicylic acid may contain more than one, e.g. two or three, alkyl substituents, but it is preferred that it contain only one such substituent, and that in the para position. Preferably, the number of carbon atoms in the alkyl substituent(s) is at least 14, and preferably ranges from 14 to 30. When the alkyl salicylic acid mainly contains only one alkyl substituent, the alkyl group contains most preferably from 14 to 26 carbon atoms. The alkyl group(s) could be linear or branched, but are most preferably linear. Suitable olefins include, but are not limited to, 1-tetradecene, 1-hexadecene, 1-octadecene, 1-eicosene, 1-docosene, 1-tetracosene, mixtures of the foregoing, and the like.

Commercial salicylic acid can be employed with or without further purification.

The conditions under which the reaction is carried out depend upon the nature of the olefin to be employed. Those skilled in the art will realize that, with differing olefins, varying optimum reaction conditions may, and probably will, be desirable.

The temperature at which the salicylic acid and the olefin are reacted is preferably 50° C. or more, and may suitably be in the range of from about 50° to about 200° C. The optimum temperature within this range is dependent on the carbon chain length of the olefin. Typically, for a $C_{14}$ olefin the optimum temperature is from about 100° to about 150° C., for example about 120° C.

The duration of the reaction is usually not critical. A reaction time of from about 2 to about 36 hours is usually satisfactory.

The reaction can, if desired, be carried out in a solvent, but normally no solvent is employed.

The alkyl salicylic acid can be recovered from the reaction mixture by means known in the art. For $C_{14}$ and higher alkyl salicylic acids, solvent extraction is typically used.

In a second step of the process of the present invention, the oil soluble acid is neutralized and overbased by carbonation of lime using $CO_2$ in the presence of a promoter, such as methanol, and a surfactant, e.g., alkyl salicylic acid. The reaction mixture after overbasing is filtered and solvents are removed by distillation.

Alternatively, alkyl salicylic acid can be reacted with a previously overbased alkaline earth sulfonate, e.g., calcium sulfonate, to produce alkaline earth salicylate salts comprising varying percentages of dispersed alkaline earth carbonate salts. In this method, no filtration of the end product is required, and, thus, it is commercially preferred.

The alkaline earth metal salicylate detergents prepared by the process of the present invention suitably include a calcium salicylate detergent, a magnesium salicylate detergent, or a mixture thereof.

The amount of base added should be sufficient to provide an overbased salt, i.e., one in which the ratio of the number of equivalents of the metal moiety to the number of equivalents of the alkyl salicylic acid moiety is usually greater than about 1.2, and can be as high as 4.5 or greater.

Overbased alkaline earth metal salicylates may be obtained by overbasing a neutral alkaline earth metal salicylate to produce an alkaline earth metal carbonate, such as calcium carbonate and magnesium carbonate, or an alkaline earth metal borate, such as magnesium borate.

The base number of the metal salicylate detergent is not particularly limited; however, the base number is normally in the range of from about 60 to about 350 mg KOH/g, preferably from about 150 to about 350 mg KOH/g.

The metal base may be added either in a single addition or in a plurality of additions at intermediate points during the reaction.

The overbasing reaction mixture suitably further contains a promoter, preferably an oxygen-containing organic solvent and optionally water. Suitable promoters include $C_{1-6}$ alcohols, polyhydric alcohols such as glycol, propylene glycol, glycerol or 1,3-dihydroxypropane, ethers such as $C_{1-4}$ monoethers of glycol or propylene glycol, diisopropyl ether, 1,3- or 1,4-dioxane, or 1,3-dioxolane. Preferably the promoter is a $C_{1-6}$ alcohol, in particular, methanol.

The solvent for the reaction of the alkyl salicylic acid with the metal base may be (1) a polyhydric alcohol having 2 to 4 carbon atoms;
(2) a di-($C_2$ to $C_4$) glycol;
(3) a tri-($C_2$ to $C_4$) glycol;
(4) a mono- or polyalkylene glycol alkyl ether of the formula:

$$R^1(OR^2)_xOR^3$$

wherein $R^1$ is a $C_1$ to $C_6$ alkyl group, $R^2$ is an alkylene group, $R^3$ is hydrogen or a $C_1$ to $C_6$ alkyl group and x is an integer from 1 to 6;
(5) a monohydric alcohol having up to 20 carbon atoms;
(6) a ketone having up to 20 carbon atoms;
(7) a carboxylic acid ester having up to 10 carbon atoms;

(8) a volatile liquid hydrocarbon; or (9) an ether having up to 20 carbon atoms.

The preferred solvent is an inert hydrocarbon, which can be either aliphatic or aromatic. Suitable examples include toluene, xylene, naphtha, and aliphatic paraffins, e.g., hexane, and cycloaliphatic paraffins.

A combination of methanol, which acts as a promoter in the reaction, and naphtha is especially preferred.

In view of the intended use of the overbased product as a lubricating oil additive, it is preferred to incorporate a base oil as a supplemental diluent. The base oil can be an animal oil, a vegetable oil, or a mineral oil. Preferably, it is a petroleum-derived lubricating oil, such as a naphthenic base, a paraffin base, or a mixed base oil. Alternatively, the lubricating oil may be a synthetic oil, for example, a synthetic ester or a polymeric hydrocarbon lubricating oil.

Carbon dioxide can be employed in the production of overbased metal salts in the form of a gas or a solid, preferably in the form of a gas, wherein it can be blown through the reaction mixture. Carbon dioxide addition is typically effected after the addition of metal base.

A carbonation catalyst can be used to produce highly overbased metal salts. The catalyst can be either an inorganic compound or an organic compound, preferably an inorganic compound. Suitable inorganic compounds include hydrogen halides, metal halides, ammonium halides, metal alkanoates, ammonium alkanoates or mono-, di-, tri- or tetra-alkyl ammonium formates or alkanoates. Examples of suitable catalysts include calcium chloride, ammonium chloride, calcium acetate, ammonium acetate, zinc acetate, and tetramethyl(ammonium acetate). The catalyst is typically employed at a level of up to about 2% by weight. A more complete description of the production of highly overbased metal alkyl salicylates can be found in EP-A-0351052.

Suitably the elevated temperature employed in the above reaction may be in the range from about 100° to about 500° F. (about 38° to about 260° C.).

The concentrate of the metal salt in the solvent can be recovered by conventional means, such as distillative stripping. Finally, the concentrate can be filtered, if desired.

In general, the process of preparing the overbased calcium salicylates comprises reacting a solution of alkylated salicylic acids and, optionally, calcium sulfonate or sulfonic acid (for convenience, the following discussion will focus on calcium compounds, but those skilled in the art will readily comprehend that, by analogy, the process can be applied to magnesium compounds, as well as to calcium and magnesium mixtures) in oil with a slurry of calcium oxide or hydroxide and bubbling carbon dioxide through the reaction mixture, thereby incorporating an excess of calcium carbonate into the calcium salicylate and, if present, calcium sulfonate, which confers the desired reserve alkalinity to the product. In this process, it has been found advantageous to add a low molecular weight alcohol, such as methanol, and water to promote the formation of a micellar dispersion of calcium carbonate.

Calcium hydroxide when used commercially as the sole reserve alkalinity agent in the reaction mixture is used in substantial excess in order to achieve a high TBN product.

A dispersant is an optional component of the process and product for the overbased detergent. One useful dispersant is the reaction product of hydrocarbyl-substituted succinic acid or anhydride with amines containing at least one primary or secondary amino nitrogen, e.g., the polyalkylene polyamines fulfill this requirement as do the substituted polyalkylene polyamines, and for that matter, ammonia. The bis-succinimides are also useful as optional dispersants. The bis-succinimides are prepared by the reaction of hydrocarbyl-substituted succinic acid or anhydride with an amine containing at least two primary and/or secondary nitrogens. Such bis-succinimides are, for example, the polyisobutenyl bis-succinimides of ethylene diamine, diethylene triamine, or triethylene tetramine, or tetraethylene pentamine or N-methyldipropylene triamine, etc. (e.g., Benoit, U.S. Pat. No. 3,438,899). The various above-described dispersing agents can be used alone or in mixtures.

The overbased calcium salicylate product of the present invention has an amorphous micellar structure. The overbased calcium salicylate, or like overbased detergent, is a stable dispersion of amorphous calcium carbonate.

The overbased calcium salicylate detergent of the present invention may be added to engine or lubricating oils in detergent amounts of about 0.1 to 25% by weight or more.

The present invention is applicable to a wide variety of lubricating oils. The lubricating oil can be composed of one or more natural oils, one or more synthetic oils, or mixtures thereof. Natural oils include animal oils and vegetable oils (e.g., castor, lard oil), liquid petroleum oils, and hydrorefined, solvent-treated or acid-treated mineral lubricating oils of the paraffinic, naphthenic and mixed paraffinic types. Oils of lubricating viscosity derived from coal or shale are also useful base oils.

Synthetic lubricating oils include hydrocarbon oils and halo-substituted hydrocarbon oils, such as polymerized and interpolymerized olefins (e.g., polybutylenes, polypropylenes, propylene-isobutylene copolymers, chlorinated polybutylenes, poly(1-hexenes), poly (1-octenes), poly(1-decenes)); alkylbenzenes (e.g., dodecylbenzenes, tetradecylbenzenes, dinonylbenzenes, di(2ethylhexyl)benzenes); polyphenyls (e.g. biphenyls, terphenyls, alkylated polyphenols); alkylated diphenyl ethers and alkylated diphenyl sulfides and the derivatives, analogs, and homologs thereof.

Alkylene oxide polymers and interpolymers and derivatives thereof where the terminal hydroxyl groups have been modified by esterification, etherification, etc., constitute another class of known synthetic lubricating oils. These are exemplified by polyoxyalkylene polymers prepared by polymerization of ethylene oxide or propylene oxide, the alkyl and aryl ethers of these polyoxyalkylene polymers (e.g., methylpolyisopropylene glycol ether having an average molecular weight of 1000, diphenyl ether of polyethylene glycol having a molecular weight of 500–1000, diethyl ether of polypropylene glycol having a molecular weight of 1000–1500); and mono- and polycarboxylic esters thereof, for example, the acetic acid esters, mixed $C_3$–$C_8$ fatty acid esters and $C_{13}$ oxo acid diesters of tetraethylene glycol.

Another suitable class of synthetic lubricating oils comprises the esters of dicarboxylic acids (e.g., phthalic acid, succinic acids, alkyl succinic acids and alkenyl succinic acids, maleic acid, azelaic acid, suberic acid, sebacic acid, fumaric acid, adipic acid, linoleic acid dimer, malonic acid, alkylmalonic acids, alkenyl malonic acids) with a variety of alcohols (e.g., butyl alcohol, hexyl alcohol, dodecyl alcohol, 2-ethylhexyl alcohol, ethylene glycol, diethylene glycol monoether, propylene glycol). Specific examples of these esters include dibutyl adipate, di-(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, and the complex ester formed by reacting one mole of sebacic acid with two moles of tetraethylene glycol and two moles of 2-ethylhexanoic acid.

Esters useful as synthetic oils also include those made from $C_5$ to $C_{12}$ monocarboxylic acids, and polyols and polyol ethers such as neopentyl glycol, trimethylolpropane, pentaerythritol, dipentaerythritol, and tripentaerythritol.

Silicon-based oils such as the polyalkyl-, polyaryl-, polyalkoxy-, and polyaryloxysiloxane oils and silicate oils comprise another useful class of synthetic lubricants; they include tetraethyl silicate, tetraisopropyl silicate, tetra-(2-ethyhexyl)silicate, tetra-4-methyl-2-ethylhexyl) silicate, tetra-(p-tert-butyphenyl) silicate, hexa-(4-methyl-2-pentoxy) disiloxane, poly(methyl)siloxanes and poly(methylphenyl) siloxanes. Other synthetic lubricating oils include liquid esters of phosphorus-containing acids (e.g., tricresyl phosphate, trioctyl phosphate, diethyl ester of decylphosphonic acid) and polymeric tetrahydrofurans.

Unrefined, refined, and rerefined oils can be used in the lubricants of the present invention. Unrefined oils are those obtained directly from a natural or synthetic source without further purification treatment. For example, a shale oil obtained directly from retorting operations, a petroleum oil obtained directly from distillation or ester oil obtained directly from an esterification process and used without further treatment would be an unrefined oil. Refined oils are similar to the unrefined oils except they have been further treated in one or more purification steps to improve one or more properties. Many such purification techniques, such as distillation, solvent extraction, acid or base extraction, filtration, and percolation are known to those skilled in the art. Rerefined oils are obtained by processes similar to those used to obtain refined oils, but applied to oils that have been already in service. Such rerefined oils are also known as reclaimed or reprocessed oils and often are additionally processed by techniques for removal of spent additives and oil breakdown products.

The invention is particularly directed to engine oil formulations and additives therefor. As used herein the term "engine oil" means a lubricating oil that may be useful in an engine oil, and by way of example, includes an automotive oil or diesel engine oil. The lubricating oil compositions of the present invention are also suitable for lubrication of marine diesel engines including 4 stroke trunk piston engines and 2 stroke cross head engines.

The formulated oil should have a viscosity in the lubricating viscosity range, typically about 45 SUS at 100° F., to about 6000 SUS at 100° F. (about 38° C.). The lubricating oil also contains one or more overbased alkaline earth metal detergents, at least one of which is a metal-containing neutral and overbased salicylate based on alkyl salicylic acid as described herein. The detergent components collectively comprise an effective amount, which usually lies in a range of 0.01 wt. % up to as much as 25 wt. %, preferably 0.1–10 wt. %, more preferably 0.1 to 5.0%. Unless indicated otherwise herein, all weight percentages are by weight of the entire lubricating oil composition.

The amount of additive concentrate to be included in a finished lubricating oil will depend on the nature of the final use. For marine lubricating oils, it is typically enough to provide a TBN of from 9 to 100; for automobile engine lubricating oils enough to provide a TBN of from 4 to 20.

As used herein, the term "Total Base Number" or "TBN" refers to the amount of base equivalent to milligrams of KOH in 1 gram of additive. Thus, higher TBN numbers reflect more alkaline products and therefore a greater alkalinity reserve. The Total Base Number for an additive composition is readily determined by ASTM test method number D2896 or other equivalent methods.

The finished lubricating oil can also contain effective amounts of one or more other types of conventional lubricating oil additives, for example, viscosity index improver, antiwear agent, antioxidant, dispersant, rust inhibitor, pourpoint depressants, and the like.

The advantages and the important features of the present invention will be more apparent from the following examples.

EXAMPLES

Example 1

Alkylation of Salicylic Acid

Salicylic acid (215.0 grams) is added to a 3 liter glass vessel equipped with stirrer and thermometer and heating mantle. A mixed $C_{14}$–$C_{18}$ olefin (367.7 grams) is added next, followed by an alkylation catalyst, such as 45.1 grams of methanesulfonic acid. The mixture is heated to 120° C. and kept at that temperature for 24 hours. Next, some VM&P naphtha (582.6 grams) is introduced and the clear solution is allowed to settle to remove the spent catalyst. The product recovered is a clear yellowish naphtha diluted alkyl salicylic acid suitable for direct overbasing or for reaction with previously overbased detergent.

Example 2

Calcium Salicylate Preparation 35 grams of a 500 TBN calcium sulfonate is added to a reaction vessel that contains 20 grams of VM&P naphtha, 15 grams of base oil, and 20 grams of methanol. Once thoroughly mixed, 100 grams of the alkyl salicylic acid described in Example 1 is added slowly and the temperature is increased to 420° F. (about 216° C.) over the next 2 hours. The stripped calcium salicylate is bright and clear, with a viscosity of 45 centistokes, TBN of 170 and % calcium of 6.1%.

The product of Example 2 has been tested in PDSC (Pressure Differential Scanning Calorimetry) and found to have an induction time of 109 minutes. A corresponding calcium sulfonate had an OIT of less than 30 minutes.

The same product has been tested for high temperature detergency using a panel coker test and found to have 3.5 milligrams deposit. A corresponding overbased sulfonate used as a source of base ($CaCO_3$) in the above reaction had 75 milligrams deposit.

The Panel Coker Test is a procedure for determining the tendency of oils to form solid decomposition products when in contact with surfaces at elevated temperatures. The test can be performed with a Falex Panel Coking Test Apparatus, which is designed to perform Federal Test Standard 791 B, Method 3462.

Example 3

Calcium Salicylate Preparation

One hundred and forty grams of the alkyl salicylate prepared as in Example 1 is added to a reactor, followed by 50 grams of base oil, 220 grams of VM&P naphtha, nine grams of methanol, 7.5 grams of neutral calcium sulfonate and 23 grams of hydrated lime. The mixture is heated to 140° F. (60° C.) and $CO_2$ is introduced until the lime is converted to $CaCO_3$. The reaction mixture is filtered and distilled to produce a fluid, bright, and clear calcium salicylate detergent.

PDSC testing showed an OIT of 140 minutes while the Panel Coker Test demonstrated excellent detergency with 8.5 milligrams deposit.

Example 4

Calcium Salicylate Preparation

Comparative Example

The reaction of alkyl salicylic acid with the overbased sulfonate requires precise conditions, otherwise undesirable crystalline calcium carbonate is formed. The conditions of reaction shown below produced a finished salicylate that contained predominately the vaterite form of $CaCO_3$.

The conditions were identical to Example 2 except that 20 grams of water was included in addition to the 20 grams of methanol. The increased polarity destabilized the surfactant colloid and resulted in conversion of amorphous oil soluble $CaCO_3$ to crystalline vaterite. The finished product was viscous and very cloudy and not suitable for use.

In view of the many changes and modifications that can be made without departing from principles underlying the invention, reference should be made to the appended claims for an understanding of the scope of the protection to be afforded the invention.

What is claimed is:

1. A process for producing alkaline earth metal salicylates comprising the steps of:
   A) alkylating salicylic acid with a linear α-olefin comprising at least 14 carbon atoms in the presence of a strong acid catalyst to form an oil soluble alkylated salicylic acid;
   B) neutralizing the oil soluble alkylated salicylic acid;
   C) overbasing the oil soluble alkylated salicylic acid by carbonation of lime using $CO_2$ in the presence of a promoter and a surfactant;
   D) filtering the product of C); and
   E) removing solvents by distillation.

2. The process of claim 1 wherein the strong acid catalyst is anhydrous methanesulfonic acid.

3. The process of claim 1 wherein the alkylation step is carried out at a temperature in the range of from about 50 to about 200° C.

4. The process of claim 1 wherein the linear α-olefin is selected from the group consisting of 1-tetradecene, 1-hexadecene, 1-octadecene, 1-eicosene, 1-docosene, 1-tetracosene, and mixtures of the foregoing.

5. A process for producing alkali metal or alkaline earth metal salicylates comprising the steps of:
   A) alkylating salicylic acid with a linear α-olefin comprising at least 14 carbon atoms in the presence of a strong acid catalyst to form an oil soluble alkylated salicylic acid;
   B) reacting the oil soluble alkylated salicylic acid with a previously overbased detergent selected from the group consisting of overbased alkali or alkaline earth sulfonates, phenates, or carboxylates to produce alkali or alkaline earth salicylate salts comprising varying percentages of dispersed alkali or alkaline earth carbonate salts.

6. The process of claim 5 wherein the strong acid catalyst is anhydrous methanesulfonic acid.

7. The process of claim 5 wherein the alkylation step is carried out at a temperature in the range of from about 50 to about 200° C.

8. The process of claim 5 wherein the linear α-olefin is selected from the group consisting of 1-tetradecene, 1-hexadecene, 1-octadecene, 1-eicosene, 1-docosene, 1-tetracosene, and mixtures of the foregoing.

9. The process of claim 5 wherein the overbasing step is carried out it the presence of a promoter.

* * * * *